US00PP18880P2

(12) United States Plant Patent
Korlipara

(10) Patent No.: US PP18,880 P2
(45) Date of Patent: Jun. 3, 2008

(54) ***COREOPSIS* PLANT NAMED 'PINWHEEL '**

(50) Latin Name: *Coreopsis hybrid(Coreopsis, Limerock Ruby mutant×Coreopsis auriculata*
Varietal Denomination: Pinwheel

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 45 days.

(21) Appl. No.: 11/638,239

(22) Filed: Dec. 12, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Annette H Para
(74) *Attorney, Agent, or Firm*—Klarquist Sparkman, LLP

(57) ABSTRACT

A new and distinct *Coreopsis* plant named 'Pinwheel' characterized by large daisy-type flowers that are about 4 cm in diameter, ray florets that are quilled or tubular rather than flat, deep green foliage, light yellow flower color, very free branching, very free flowering, and a mounding habit.

1 Drawing Sheet

Botanical denomination: *Coreopsis* hybrid (*Coreopsis* 'Limerock Ruby' mutant×*Coreopsis auriculata*).
Variety designation: 'Pinwheel'.

BACKGROUND OF THE INVENTION

The present invention relates to a new and distinct hybrid of *Coreopsis* and given the cultivar name 'Pinwheel'. *Coreopsis* is in the family Asteraceae. This new cultivar originated from a controlled cross between a proprietary, unreleased mutant of *Coreopsis* 'Limerock Ruby' (U.S. Plant Pat. No. 15,455) and *Coreopsis auriculata,* an unpatented plant, as the pollen parent.

SUMMARY OF THE INVENTION

The following traits have been repeatedly observed and are determined to be the unique characteristics of 'Pinwheel'. These characteristics in combination distinguish 'Pinwheel' as a new and distinct cultivar:

1. Large daisy-type flowers that are about 4 cm in diameter.
2. Ray florets that are quilled or tubular rather than flat.
3. Deep green foliage.
4. Light yellow flower color.
5. Very free branching.
6. Very free flowering.
7. Mounding habit.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

DETAILED PLANT DESCRIPTION

Figure 1:
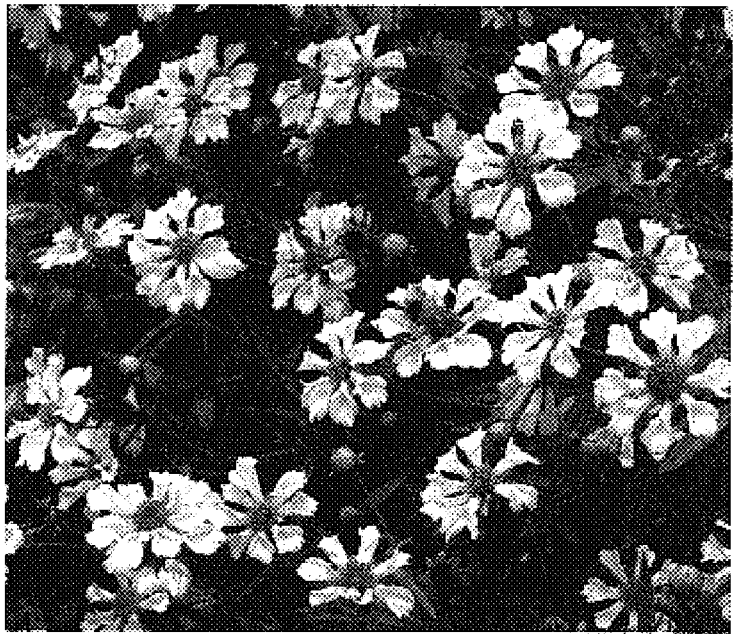
FIG. 1 shows a close up one year old *Coreopsis* 'Pinwheel,' growing in the ground in the trial field in August in Canby, Oreg.
Figure 2:
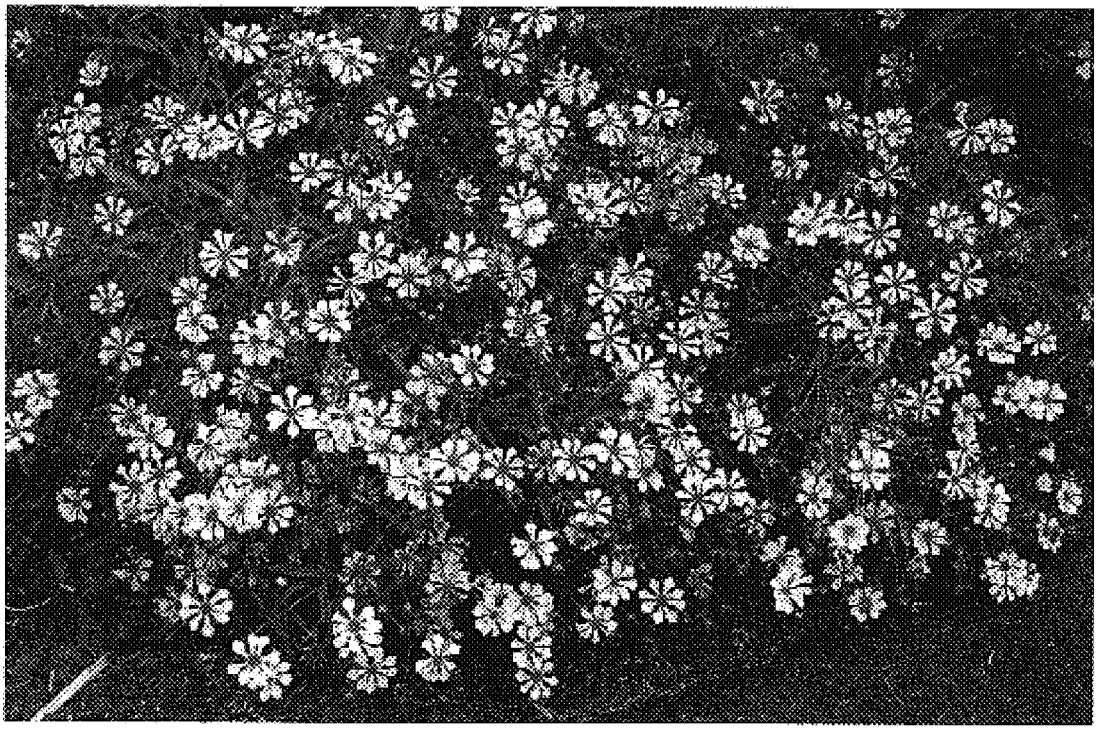
FIG. 2 shows a whole plant growing in the ground in the garden in September in Canby, Oreg.

The following is a detailed description of the new *Coreopsis* cultivar based on observations of a one-year-old specimen growing in the ground in full sun under typical outdoor conditions in the trial fields in August in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zones 5 to 9.
- *Size.*—70 cm wide and 52 cm tall to top of flowers.
- *Form.*—Mound.
- *Vigor.*—Excellent.
- *Roots.*—Fibrous, Grey Brown 199D, stems root easily from stem tip cuttings.

Stem:
- *Type.*—Ascending.
- *Size.*—43 cm tall and 6 mm wide.
- *Internode length.*—5 to 6.5 cm.
- *Surface.*—Pubescent.
- *Color.*—Green 138B.

Leaf:
- *Type.*—Compound, odd pinnate.
- *Shape.*—Ovate in outline.
- *Lobing.*—2 to 5 pinnatifid, linear to lanceolate, terminal lobe the largest (to twice as wide and ⅓ longer than side lobes), each lobe 4 to 20 mm wide and 1 to 6 cm long.
- *Arrangement.*—Opposite.

*Length including petiole.*—Variable, 19 to 5.5 cm, basal leaves can grow to 29.5 cm, leaf size decreases towards stem tip.

*Width.*—Variable, 3 to 9 cm.

*Margins.*—Entire.

*Apex.*—Acute.

*Surface texture.*—Pubescent, feels felt-like to the touch.

*Venation.*—Pinnate.

*Color.*—Top side — Yellow Green 147B. Bottom — Yellow Green 147B.

Inflorescence:

*Type.*—Long stalked terminal heads of daisy-type flowers.

*Peduncles.*—8.5 cm tall and 1 mm wide, glabrous, Yellow Green 147B.

*Size.*—Grows to 4.3 cm wide and 11 mm deep.

Florets:

*Type.*—Zygomorphic.

*Ray florets.*—7 to 8 in number, 2 cm long and 1 cm wide, ligulate with an enlarged tube, the 3-4 notched lobe is reflexed, entire, slightly undulate, 1 cm long and 1 cm wide; tube is 1 cm long and 4 mm wide; at top of tube, in front, there is usually a small limb or lobe giving a slightly frilled look; glabrous; color outside is Yellow 11A, inside Yellow 10A, no pistil or stamen.

*Cone description.*—Slightly rounded, 10 mm wide and becoming 4 mm deep with maturity, Yellow Orange 23A.

*Disc florets.*—7 mm long and 1 mm wide, corolla tubular, 3 mm long, Orange 23A at the apex to Yellow Orange 17C near base, Pistil — 7 mm long, ovary 1.5 mm long and Yellow Green 149D, style 5.5 mm long; stigma extruding, 2-branched, Orange 23A. Stamen — anthers 2 mm long, Black 202A, filaments 1 mm long, Yellow Orange 17B, pollen none, male sterile.

*Bloom period.*—June through September in Canby, Oreg.

*Fragrance.*—Light, Chrysanthemum-like.

Seed: None produced.

*Fertility.*—Infertile.

Disease and pests: *Coreopsis* are susceptible to mildew and fungal spots. No resistance is known for this variety.

COMPARISONS TO SIMILAR *COREOPSIS*

Compared to *Coreopsis auriculata,* the pollen parent, this new cultivar has light yellow rather than yellow orange flower color.

Compared to *Coreopsis* 'Limerock Ruby' mutant, the seed parent, the new variety has light yellow flower color rather than ruby red.

I claim:

1. A new and distinct *Coreopsis* plant as herein illustrated and described.

* * * * *